US007399630B2

(12) United States Patent
Guarino et al.

(10) Patent No.: US 7,399,630 B2
(45) Date of Patent: *Jul. 15, 2008

(54) PEPTIDES FOR ENHANCED CELL ATTACHMENT AND GROWTH

(75) Inventors: Richard David Guarino, Holly Springs, NC (US); Bryce Nelson Chaney, Durham, NC (US); Andrea Liebmann-Vinson, Willow Springs, NC (US); Mohammad A. Heidaran, Cary, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/604,530

(22) Filed: Nov. 27, 2006

(65) Prior Publication Data

US 2007/0077651 A1  Apr. 5, 2007

Related U.S. Application Data

(60) Division of application No. 10/670,771, filed on Sep. 26, 2003, now Pat. No. 7,157,275, which is a continuation-in-part of application No. 10/641,286, filed on Aug. 15, 2003, now Pat. No. 7,074,615.

(51) Int. Cl.
*C12M 3/00* (2006.01)
*C12N 5/00* (2006.01)
*C12N 5/02* (2006.01)
*C12N 5/06* (2006.01)
*C07K 17/08* (2006.01)

(52) U.S. Cl. ............. 435/289.1; 435/402; 435/404; 530/330; 530/402

(58) Field of Classification Search ........... 435/325, 435/240, 243, 289.1; 530/330, 402
See application file for complete search history.

(56) References Cited

U.S. PATENT DOCUMENTS

| 4,851,521 | A  | 7/1989  | della Valle      |
| 5,278,063 | A  | 1/1994  | Hubbel et al.    |
| 6,150,459 | A  | 11/2000 | Mayes et al.     |
| 2003/0022152 | A1 | 1/2003 | Campbell et al. |
| 2003/0113812 | A1 | 6/2003 | Hemperly        |
| 2003/0113813 | A1 | 6/2003 | Heidaran et al. |
| 2003/0162289 | A1 | 8/2003 | Campbell et al. |
| 2003/0175745 | A1 | 9/2003 | Dean et al.     |

FOREIGN PATENT DOCUMENTS

WO    WO 02/02591    1/2002

OTHER PUBLICATIONS

Brandley et al., *Analytical Biochemistry*, 1988, pp. 270-278, vol. 172.
Choi et al., *Biomaterials*, 1999, pp. 409-417, vol. 20.
Couchman et al., *J. Call Blot.*, 1982, pp. 402-410, vol. 93.
Elbert et al., *Anna. Rev. Meter. Set.*, 1995, pp. 385-394, vol. 28.
Fukai et al., *Biochemistry*, 1983, pp. 5746-5751, vol. 32.
Glass et al., *Ann N Y Acad Sct*, 1994, pp. 177-185, vol. 745.
Glass et al., *Biomaterials*, 1996, pp. 1101-1108, vol. 17.
Grinnell, F., *Int. Rev. Cytol.*, 1978, pp. 65-144, vol. 53.
Grzesiak et al., *Biomaterials*, 1997, pp. 1625-1632, vol. 18 (24).
Grzeski et al., *Journal of Bone and Mineral Research*, 1994, pp. 487-496, vol. 9(4).
Gutsche et al., *Biomaterials*, 1996, pp. 387-393, vol. 17.
Healy et al., *Annals Now York Academy of Sciences*, 1999, pp. 24-35, vol. 875.
Hern et al., *J. Blomed. Mater, Res.*, 1993, pp. 266-276, vol. 39.
Hubbell, J.A., *Biotechnology*, 1995, pp. 565-576, vol. 13.
Hyun et al., *Langmuir*, 2002, pp. 2975-2979, vol. 18 (8).
Kantlehner et al., *Chembiochem*, 2000, pp. 107-114, vol. 1 (2).
Kim et al., *Ann. Surgery*, 1998, pp. 8-13, vol. 228.
Kleinman, et al., *Biochem. Biophys. Res. Commun.*, 1976, pp. 426-432, vol. 72.
Kobayashi et al., *Curr Eye Res*, 1991, pp. 899-908, vol. 10 (10).
Lin et al., *J. Biomater. Sci. Polymer Edn.*, 1992, pp. 217-227, vol. 3(3).
Lu et al., *Biomaterials*, 2000, pp. 1595-1605, vol. 21.
Madihally et al., *Biomaterials*, 1999, pp. 1133-1142, vol. 20.
Mann et al., *J Biomed Meter Res*, 2002, pp. 86-93, vol. 60(1).
Marchand-Brynaert et al., *Biomaterials*, 1999, pp. 1773-1782, vol. 20.
Massia et al., *Ann N Y Acad Sci*, 1990, pp. 261-270, vol. 589.
Massia at al, *J Cell Biol*, 1991, pp. 1089-1100, vol. 114 (5).
Massia et al., *J Biomed Meter Res*, 2001, pp. 390-399, vol. 56 (3).
Mertz et al., *J Burn Care Rehabil*, 1996, pp. 199-206, vol. 17 (3).
Myles et al., *J, Biomater. Sci. Polymer Edn*, 2000, pp. 69-86, vol. 11 (1).
Neff et al., *J. Biomed. Mater. Res.*, 1996, pp. 511-519, vol. 40.
Olivieri et al., *J. Biomed. Meter. Res.*, 1999, pp. 355-369, vol. 46.
Oxley at al., *Biomaterials*, 1993, pp. 1064-1072, vol. 14.
Patel et al., *J Biomater Sci Polym Ed*, 2000, pp. 319-331, vol. 11 (3).
Pearlstein, E., *Nature*, 1976, pp. 497-500, vol. 262.
Pieper et al., *Biomaterials*, 1999, pp. 947-966, vol. 20.
Pierschbacher et al., *J Cell Biochem*, pp. 150-154, vol. 1994, 56 (2).
Pinilla et al., *Meth. Molec, Biol.*, 1996, pp. 171-179, vol. 66.

(Continued)

*Primary Examiner*—Maryam Monshipouri
*Assistant Examiner*—Marsha M Tsay
(74) *Attorney, Agent, or Firm*—Alston & Bird LLP

(57) ABSTRACT

The present invention relates to cell adhesion promoting ("CAP") peptide combinations that promote cell attachment or cell adhesion to culture surfaces that are otherwise cell adhesion resistant "CAR". The invention provides combination of peptides that, when covalently coupled to a CAR layer such as hyaluronic acid that has been created on a polystyrene surface, promote cell attachment, growth differentiation, and execution of other desired cellular functions in culture.

16 Claims, 5 Drawing Sheets

OTHER PUBLICATIONS

Porte-Durrieu et al., *J. Biomed. Mater. Res.*, 1999, pp. 3613-3675, vol. 46.
Ranucci et al., *Tissue Engineering*, 1999, pp. 407-420, vol. 5.
Ratner. B.D., *Journal of Molecular Recognition*, 1995, pp. 617-625, vol. 9.
Rezania et al., *Biotechnol. Prog.*, 1999, pp. 19-32, vol. 15.
Rezania et al., *J Orthop Res*, 1999, pp. 615-623, vol. 17 (4).
Roberts et al., *J. Am. Chem. Soc.*, 1998, pp. 8548-8555, vol. 120 (28).
Ruoslahti et al., *Science*, 1987, pp. 491-497, vol. 238 (4626).
Saad et al., *J. Biomed. Res.*, 1996, pp. 355-366, vol. 32.
Schense et al., *J Biol Chem*, 2000, pp. 6813-6818, vol. 275 (10).
Singer et al., *J. Cell Biol.*, 1987, pp. 573-584, vol. 104.
Sugawara et al., *J. Biomed. Mater. Res.*, 1995, pp. 1047-1052, vol. 29.
Torres et al., *Biomaterials*, 2000, pp. 1607-1619, vol. 21.
Vogler, E.A., *Journal of Biomedical Materials Research*, 1987, pp. 1197-1211, vol. 21.
Whang et al., *Polymer*, 1995, pp. 837-842, vol. 36.
Zhang et al., *J. Biomed. Mater. Res.*, 1999, pp. 285-293, vol. 45.

Figure 4 CYP activity using Individual Peptides
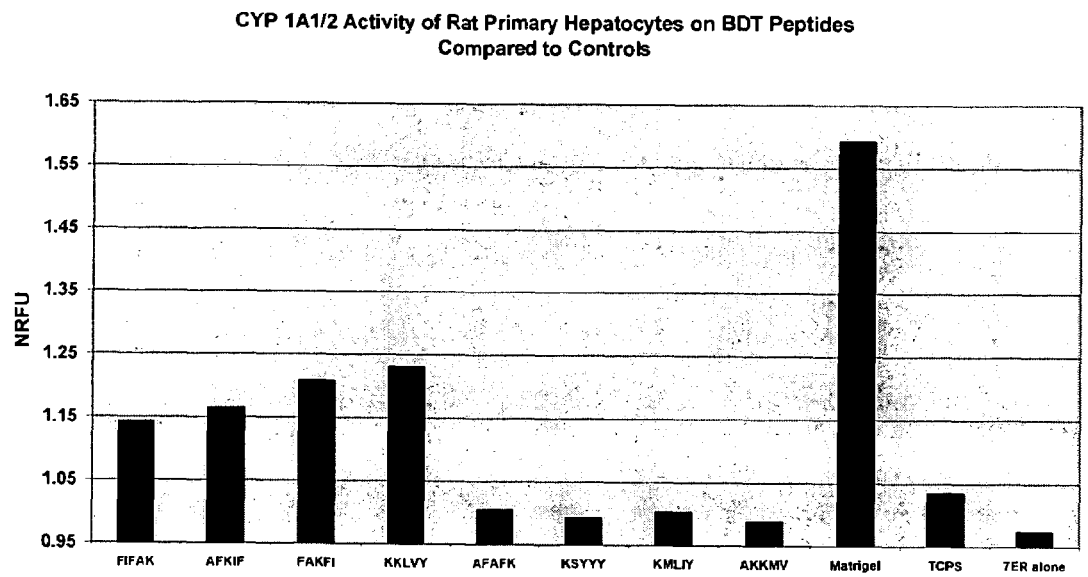
Figure 5 Albumin secretion using Individual Peptides
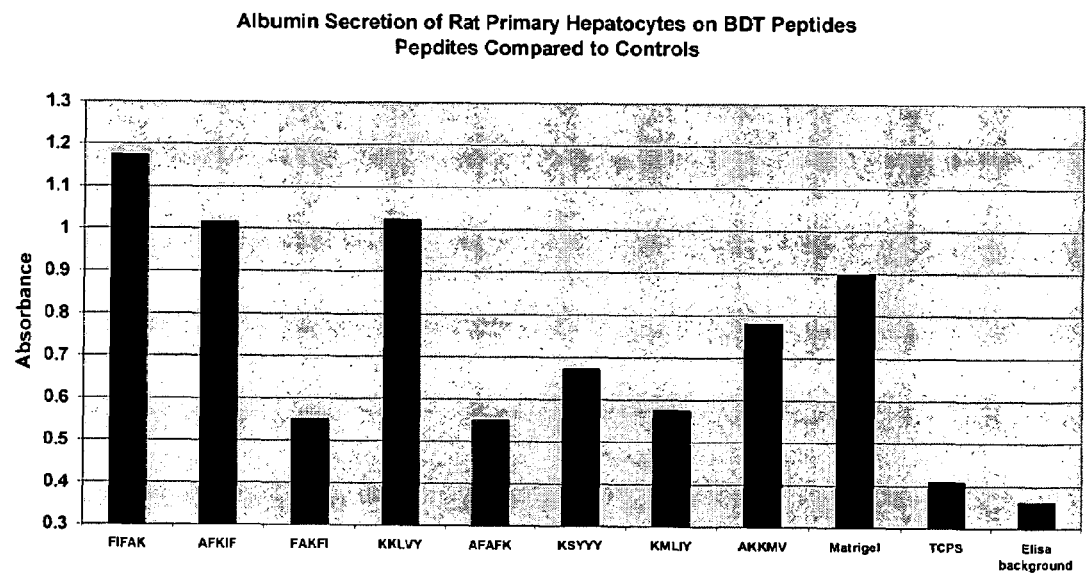

Figure 6 CYP activity using multiple peptides
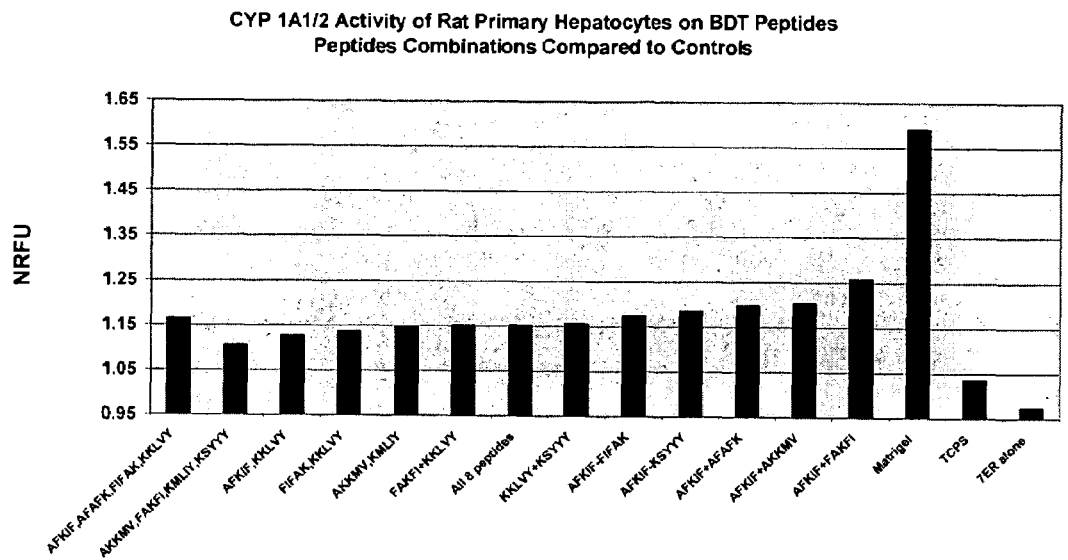
Figure 7 Albumin secretion activity using multiple peptides
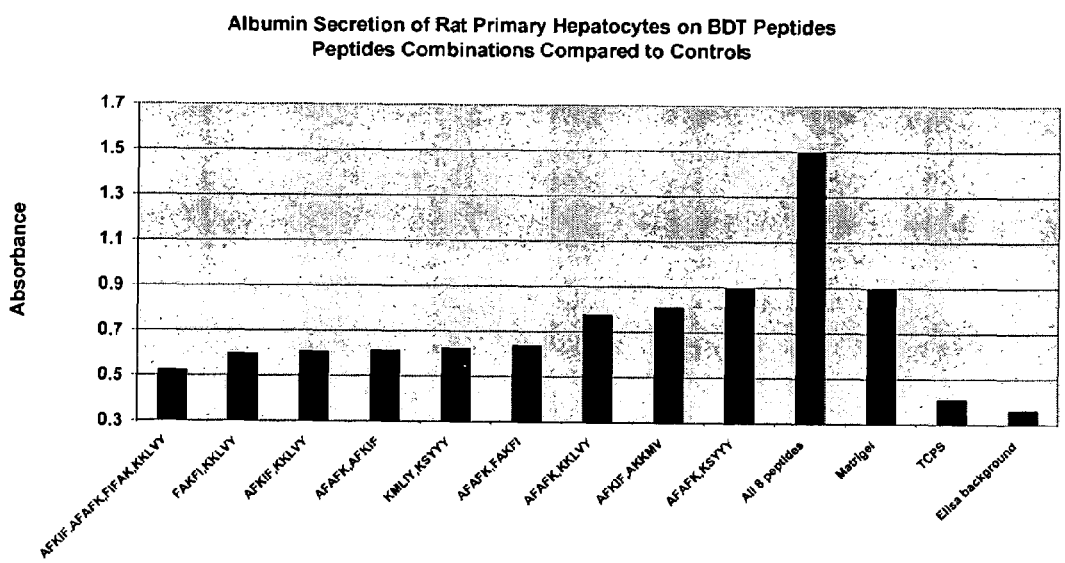

SEQUENCE LISTING

```
<160> NUMBER OF SEQ ID NOS: 44

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Phe Ile Lys Phe Gly
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Phe Ile Lys Tyr
1               5

<210> SEQ ID NO 3
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 3

Glu Glu Glu Lys Val
  1               5

<210> SEQ ID NO 4
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly His Lys
  1

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Phe Ile Phe Ala Lys
  1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Lys Leu Val Tyr
  1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Phe Lys Ile Phe
  1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Phe Ala Phe Lys
  1               5
```

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Phe Ala Lys Phe Ile
 1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Met Leu Ile Tyr
 1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Lys Ser Tyr Tyr Tyr
 1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Lys Lys Met Val
 1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Phe Lys Phe Ile Gly
 1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 14

Ala Phe Ile Pro Val
 1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Lys Met Tyr Tyr
 1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Ile Lys Lys Lys
 1               5

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Arg Gly Asp
 1

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Tyr Ile Gly Ser Arg
 1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Arg Glu Asp Val
 1               5

<210> SEQ ID NO 20
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 20

Tyr Ile Gly Ser Arg
  1               5

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Glu Asp Val
  1

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Arg Gly Asp Ser
  1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Lys Ile Phe Phe
  1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Ala Ile Lys Lys
  1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ile Lys Tyr Tyr Tyr
  1               5
```

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Lys Phe Ala Phe Ile
 1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Phe Ile Lys Leu Met
 1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Phe Phe Phe Ile Lys
 1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Glu Phe Ile Lys Lys
 1               5

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gln Val Val Ala Lys
 1               5

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 31

Asn Thr Val Tyr Tyr
 1               5

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Pro Val Val Tyr
 1               5

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Lys Lys Lys Lys
 1

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ile Phe Phe Lys Gly
 1               5

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Lys Asn Ser Thr
 1               5

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Asp Asp Glu Glu Lys
 1               5

<210> SEQ ID NO 37
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ala Phe Phe Lys Ile
 1               5

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ala Lys Lys Lys Thr
 1               5

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Ala Asp Met Gln
 1               5

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Phe Lys Leu Val Ala
 1               5

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Val Phe Pro Phe Lys
 1               5

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Phe Phe His Pro Tyr
```

-continued

```
<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Asp Ile Lys Pro Val
  1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Lys Leu Leu Met Val
  1               5
```

PEPTIDES FOR ENHANCED CELL ATTACHMENT AND GROWTH

CROSS-REFERENCE TO RELATED PATENT APPLICATIONS

This application is a divisional of U.S. patent application Ser. No. 10/670,771, filed Sep. 26, 2003, which is a continuation-in-part of U.S. patent application Ser. No. 10/641,286 filed Aug. 15, 2003, now U.S. Pat. No. 7,074,615, each of which is hereby incorporated in its entirety by reference herein.

BACKGROUND OF THE INVENTION

The present invention relates to peptides that affect the biological activity of cells in culture. In particular, the invention is directed to specific peptide combinations and compositions thereof which promote the attachment and growth of cells on an otherwise cell adhesion resistant (CAR) surface.

DESCRIPTION OF THE BACKGROUND ART

Cell adhesion and cell growth in in vitro culture requires physical and chemical cues from the in vitro environment. Identification of these cues is vital to obtain control over these otherwise very arbitrary processes. Surfaces that do not support cell adhesion but that can be modified with biologically active ligands are a valuable tool to (1) study cell ligand interactions, (2) help identify components of cell culture environmental "cues" necessary for cell attachment growth, and (3) create commercially useful culture media and vessels for optimal attachment, growth, differentiation and other function of cells of any given type.

Extracellular matrix (ECM) proteins (E. D. Hay, ed., *Cell Biology of Extracellular Matrix*, $2^{nd}$ ed., Plenum Press, New York, 1991) can be used to mediate cell attachment and growth in culture. A few peptide sequences in these complex three-dimensional proteins have been identified as being responsible for cell attachment. The most prominent example is the arginine-glycine-aspartate (Arg-Gly-Asp or RGD)-peptide sequence present in the ECM protein fibronectin. Other peptide sequences may deliver signals and trigger signaling pathways within cells. Identification of such effects on cells has been the subject of intensive research.

Cells in culture are known to prefer peptides compared to their constituent amino acids as nutrients. Investigators have taken several approaches to determine which peptides are best suited for affecting growth or other biological activity of cells in vitro. Recent developments in peptide synthesis technology have enabled the production and screening of large numbers of peptides as additives to culture media either as individual defined sequences or as a mixture of different sequences in the form of a peptide library. The library approach permits screening of larger numbers of peptide sequences for desired effects in culture. Once the sequence of a peptide having the desired biological activity becomes known, it may be produced in large quantities, by chemical synthesis or by recombinant expression techniques, and formulated in a culture medium or coated on a culture substrate or surface to produce the desired effect on cultured cells.

Interactions of cells with components of the ECM in vivo is important in biological processes including cellular growth, migration, and differentiation. The ability of anchorage-dependent cells to adhere to culture surfaces largely dictates the success of a cell culture effort. In particular, the abilities of cells to adhere, spread, and contact on solid surfaces are prerequisites for the growth of normal anchorage-dependent cells in vitro (Grinnell, F., *Int. Rev. Cytology* 53:67-149, 1978; Couchman et al., *J Cell Biol.*, 93:402-410, 1982). The ability of cells to adhere to solid surfaces is affected by many factors including the cell culture media used, the particular type of cell, and the particular surface upon which the cells are cultured.

Mammalian cells are usually cultured on surfaces of polymer (plastic) culture vessels. Adhesion of mammalian cells to synthetic polymer surfaces is almost always controlled by proteins absorbed to the surfaces and is mediated by cellular receptors. For example, fibronectin, a protein of the ECM, is involved in the adhesion of mammalian cells of various types to cell culture substrates (Pearlstein, E., *Nature* 262:497-500, 1976; Kleinman, et al., Biochem. *Biophys. Res. Commun.* 72:426-432, 1976). Fibronectin's ability to promote cell attachment has been localized to a tripeptide sequence RGD present in the cell binding domain.

It is known that when a protein solution is added to a culture substrate, proteins are immediately adsorbed to the surface. Cell attachment to the substrate and subsequent spreading depend on the presence of cell surface receptors for some of the adsorbed proteins. A prerequisite is that the conformation of the adsorbed protein has not been altered too drastically (i.e., denatured) by adsorption, which might destroy any ligand structure necessary for affinity to the receptors.

If cells are seeded on a polymer substrate lacking adsorbed proteins, then proteins on the cell surface may directly adsorb to the polymer and, under suitable conditions, the cells will be stimulated to secrete proteins towards the surface, mimicking formation of an ECM. However, cultured cells do not "directly" contact the polymer surface; contact is mediated by the adsorbed proteins (Grinnell, F., Int. Rev. Cytol. 53, 65-144,1978; Vogler, E. A., Journal of Biomedical Materials Research 21, 1197-1211, 1987).

Investigators have proposed adsorbing particular peptides to a polymer surface to promote short-term cell adhesion. For example, Singer et al. proposed adsorbing an RGD-containing 13-mer peptide onto a polymer substrate (Singer, I. I. et al., *J Cell Biol.* 104:573-584, 1987).

An alternative to the foregoing approach is to attach peptides covalently to a chemically modified polymer surface. For example, Brandley et al., studied a 9-mer peptide in a polymer substrate as a stimulus to cell adhesion (Brandley et al., *Anal. Biochem.* 172:270, 1988). While this method promoted adhesion, it required large concentrations of peptide. Since the cost of preparing synthetic peptides remains high, incorporation of peptides into the bulk of the polymer would not be economical.

U.S. Pat. No. 5,278,063 to Hubbell et al. discloses surfaces derivatized with peptides shorter than 12 amino acids that include one of the following sequences: GRGD (SEQ ID NO:17), GYIGSR (SEQ ID NO:18) and GREDV (SEQ ID NO:19). These peptides were further characterized as including a "minimal" cell-surface receptor recognition sequence, RGD, YIGSR (SEQ ID NO:20), or REDV (SEQ ID NO:21), that permits engagement by the cells' receptors of the peptides derivatizing the surface. The peptides were grafted to the surface by reaction of the peptide's terminal primary amine with an active group on the polymer surface. A disadvantage of this method is the requirement for activating the surface before derivatization. The activation process can be lengthy and may involve toxic reagents, requiring thorough washing of the surface prior to modification with the peptide and prior to culturing of the cells on the derivatized surface.

Thus, a need exists in the art for relatively short peptides that can be used to modify polymer cell culture surfaces to promote cell adhesion and subsequent growth. Such peptides should be thermally stable and resistant to proteolysis by either cellular proteases or exogenously added proteases (such as trypsin) which are commonly used to dislodge adherent cells from the substrate. Such peptides should also be resistant to simple desorption from the surface of polymer substrate to which they have been bound.

SUMMARY OF THE INVENTION

The present invention is directed to peptides that enhance cell attachment to culture surfaces that are otherwise cell adhesion resistant ("CAR"). Such peptides are "cell adhesion promoting" (abbreviated herein as "CAP"). The invention provides selected peptides, and particular combinations of peptides that, when covalently coupled to a CAR layer such as hyaluronic acid (HA) that has been created on a polystyrene surface, promote cell attachment, growth, differentiation, and the execution of other desired cellular functions in culture.

The preferred peptide of this invention has a length of about 30 or fewer amino acids. In other embodiments, the preferred peptide or polypeptide has between about 25 or fewer, 20 or fewer, 15 or fewer, 10 or fewer, and more preferably 4-5 amino acids. Optionally, the peptide may comprise an amino acid having the RGD sequence.

Specific CAP peptides discovered by the present inventors include: SEQ ID NO: 1 (FIKFG), SEQ ID NO: 2 (EFIKY), SEQ ID NO: 3 (EEEKV), SEQ ID NO: 4 (GHK), SEQ ID NO: 5 (FIFAK), SEQ ID NO: 6 (KKLVY), SEQ ID NO: 7 (AFKIF), SEQ ID NO: 8 (AFAFK), SEQ ID NO: 9 (FAKFI), SEQ ID NO: 10 (KMLIY), SEQ ID NO: 11 (KSYYY), SEQ ID NO: 12 (AKKMV), SEQ ID NO: 13 (FKFIG), SEQ ID NO: 14 (AFIPV), SEQ ID NO: 15 (KKMYY), and SEQ ID NO: 16 (AIKKK) and combinations of any two or more of the peptides identified by SEQ ID NOs 1 to 16. These peptides can be used individually or in combinations.

The present invention is also directed to a peptide-modified polymer composition which promotes attachment, growth, differentiation and further function of cells on a polymer surface that is otherwise cell adhesion resistant (CAR). The composition comprises a polymer with a CAR surface to which are bonded one or more of the peptides noted above either alone or in combination.

In a preferred embodiment, the composition comprises a combination of four peptides, selected from the following groups, bonded to the CAR surface: (a) BD Factor 3, comprised of SEQ ID NO: 1 (FIKFG), SEQ ID NO: 2 (EFIKY), SEQ ID NO: 3 (EEEKV), and SEQ ID NO: 4 (GHK); (b) BD Factor 4, comprised of SEQ ID NO: 5 (FIFAK), SEQ ID NO: 6 (KKLVY), SEQ ID NO: 7 (AFKIF), and SEQ ID NO: 8 (AFAFK); (c) BD Factor 5, comprised of SEQ ID NO: 9 (FAKFI), SEQ ID NO: 10 (KMLIY), SEQ ID NO: 11 (KSYYY), and SEQ ID NO: 12 (AKKMV); and (d) BD Factor 8, comprised of SEQ ID NO: 13 (FKFIG), SEQ ID NO: 14 (AFIPV), SEQ ID NO: 15 (KKMYY), and SEQ ID NO: 16 (AIKKK); or any combination of the BD Factors (a)-(d).

Also provided is a chemically synthesized peptide multimer or concatemer comprising one or more of the above peptides, which multimer is disclosed in the Detailed Description sections below.

Another embodiment is a recombinantly produced peptide multimer comprising the above peptide or variant thereof, which multimer has the formula $(P^1-X_m)_n-P^2$, which multimer is disclosed in the Detailed Description sections below.

The invention also provides a method for producing a CAP peptide-modified polymer composition which comprises the step of treating a CAR surface with a CAP peptide or combination of peptides under conditions in which the peptides become covalently bonded to the CAR surface. Anchorage-dependent cells are then added to the foregoing composition; and allowed to attach to the peptide-modified surface.

In a method for growing such cells, the attached cells are cultured under any of a number of known or novel culture conditions with a medium that is appropriate to the type of cells in a vessel that has a peptide modified surface. An optional step of removing any non-adherent cells after the attachment phase may be employed.

The invention further provides for a cell culture system comprising the CAP peptide modified polymer composition. The CAP peptide composition may be a standard tissue culture device, or a non-standard one, such as a 3D structure, as discussed in the Detailed Description below.

The invention also provides a method of screening a test peptide or peptides for the ability to promote cell attachment, growth, differentiation, etc., after the peptide(s) has or have been covalently bonded to a CAR surface. The method includes the steps of:

(a) providing a peptide-modified polymer composition in the form of a cell culture vessel or a surface that is added to a cell culture vessel, wherein the peptide(s) modifying the polymer are the test peptide or peptides;

(b) in a parallel culture vessel, providing a negative control polymer surface that has no peptides bound thereto or is modified with negative control peptides that do not promote cell attachment, growth, etc.;

(c) adding cells in medium to the culture vessels of (a) and (b);

(d) at one or more selected time points thereafter, assessing the number of viable, adherent cells in the culture vessels, (e) determining if there is an increased number of adherent cells in the test vessel (a) compared to the negative control vessel (b)

wherein an increased number of adherent cells in the test vessel (a) compared to the negative control vessel (b) indicates that said test peptide or peptides promote cell attachment and/or growth. Assessment of attachment or growth are performed at appropriate intervals after initial seeding of the cultures using methods well-known in the art, some of which are described below.

BRIEF DESCRIPTION OF DRAWINGS

FIG. 4 illustrates CYP activity on Day 7 of cells on CAR surfaces containing covalently linked individual peptides.

FIG. 5 illustrates albumin secretion on Day 7.

FIG. 6 illustrates that peptides from FIG. 4 one can be used in combinations of two, four or eight peptides with no appreciable loss of CYP activity.

FIG. 7 illustrates that peptides from FIG. 2 one can be used in combinations of two, four or eight peptides with no appreciable loss of albumin secretion.

DETAILED DESCRIPTION OF THE INVENTION

Figure 1:
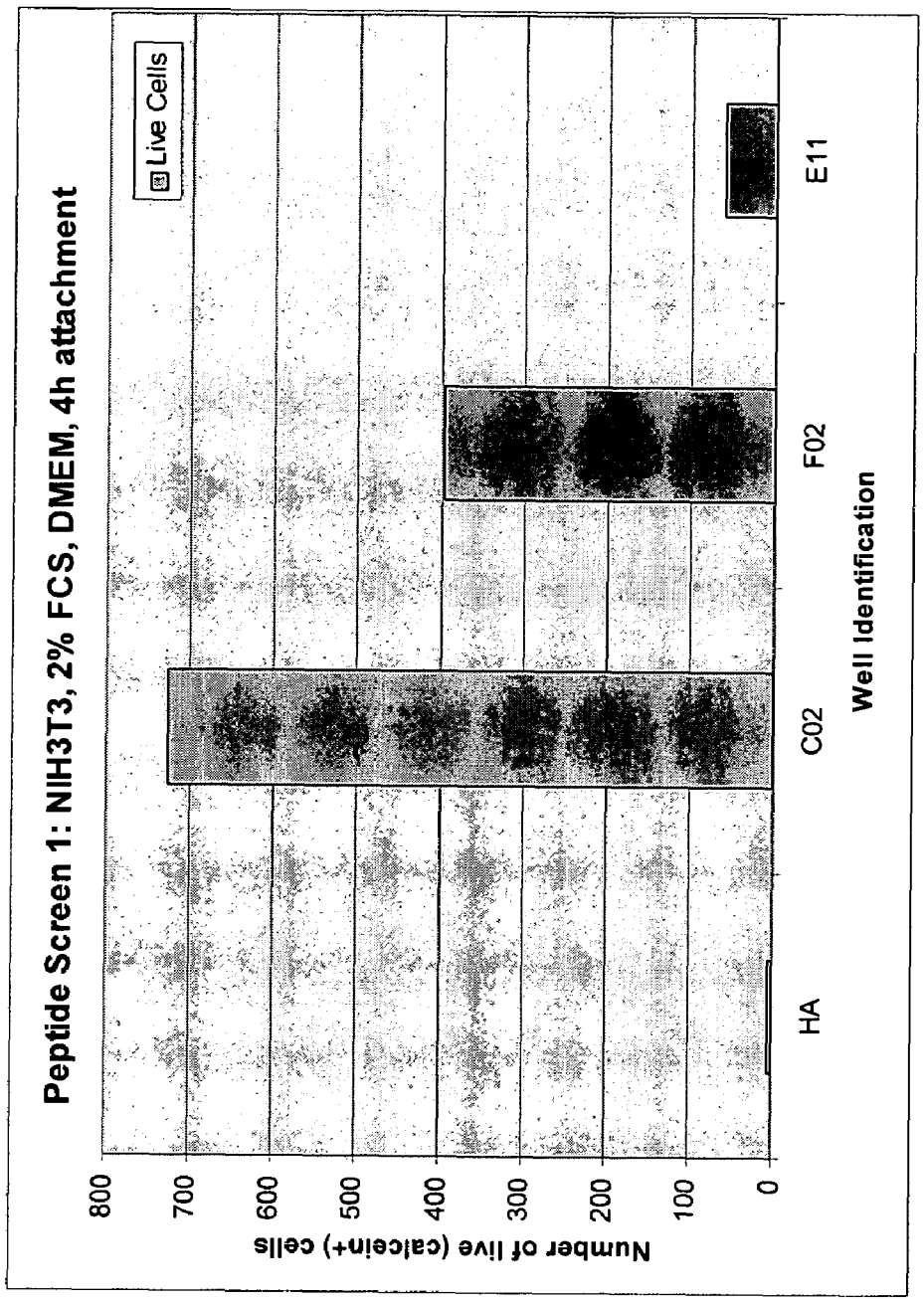
FIG. 1 is a graph showing the number of live fibroblasts attached to surfaces of HA-coated plates to which were immobilized (covalently) various combinations of peptides, as described in Example 1. Cells were assessed after four (4) hours of incubation.

The present invention provides compositions and methods for promoting attachment and growth of attachment-dependent cells by utilizing particular peptides and peptide combinations that the inventors have found to have these desired properties. As noted earlier, the present invention is focused primarily on creating a cell adhesion promoting (CAP) surface on what was otherwise a cell adhesion resistant (CAR) surface using these peptides.

The peptides of the present invention are built from repeating units of one or more of the CAP peptides described herein, namely SEQ ID NO: 1 (FIKFG), SEQ ID NO: 2 (EFIKY), SEQ ID NO: 3 (EEEKV), SEQ ID NO: 4 (GHK), SEQ ID NO: 5 (FIFAK), SEQ ID NO: 6 (KKLVY), SEQ ID NO: 7 (AFKIF), SEQ ID NO: 8 (AFAFK), SEQ ID NO: 9 (FAKFI), SEQ ID NO: 10 (KMLIY), SEQ ID NO: 11 (KSYYY), SEQ ID NO: 12 (AKKMV), SEQ ID NO: 13 (FKFIG), SEQ ID NO: 14 (AFIPV), SEQ ID NO: 15 (KKMYY), and SEQ ID NO: 16 (AIKKK). Such multimers (also termed "concatemers") may be built from any one or more of the peptides or their variants described herein. Moreover, a peptide multimer may comprise different combinations of the peptide monomers or variants thereof. Such oligomeric or multimeric peptides can be made by chemical synthesis or by recombinant DNA techniques as discussed herein. When produced by chemical synthesis, the oligomers preferably have from 2-12 repeats, more preferably 2-8 repeats of the core peptide sequence, and the total number of amino acids in the multimer preferably does not exceed about 110 residues (or their equivalents, when including linkers or spacers). Linkers can include enzymatically cleavable linkers that are known in the art. These may be engineered into a recombinant nucleic acid construct that encodes the multimer.

A preferred synthetic chemical peptide multimer has the formula $$P^1_n$$

wherein $P^1$ is selected from the group consisting of SEQ ID NO: 1 (FIKFG), SEQ ID NO: 2 (EFIKY), SEQ ID NO: 3 (EEEKV), SEQ ID NO: 4 (GHK), SEQ ID NO: 5 (FIFAK), SEQ ID NO: 6 (KKLVY), SEQ ID NO: 7 (AFKIF), SEQ ID NO: 8 (AFAFK), SEQ ID NO: 9 (FAKFI), SEQ ID NO: 10 (KMLIY), SEQ ID NO: 11 (KSYYY), SEQ ID NO: 12 (AKKMV), SEQ ID NO: 13 (FKFIG), SEQ ID NO: 14 (AFIPV), SEQ ID NO: 15 (KKMYY), and SEQ ID NO: 16 (AIKKK), shuffled sequence variants thereof (having the same amino acid composition in any and all permuted sequences) or biologically active substitution variants of these peptides, wherein n=2-10, and wherein the peptide alone or in multimeric form has the biological activity of promoting cell adhesion to an otherwise CAR surface.

In another embodiment, a preferred synthetic chemical peptide multimer has the formula $$(P^1\text{-}X_m)_n\text{-}P^2$$

wherein $P^1$ and $P^2$ are peptides independently selected from the group consisting of SEQ ID NO: 1 (FIKFG), SEQ ID NO: 2 (EFIKY), SEQ ID NO: 3 (EEEKV), SEQ ID NO: 4 (GHK), SEQ ID NO: 5 (FIFAK), SEQ ID NO: 6 (KKLVY), SEQ ID NO: 7 (AFKIF), SEQ ID NO: 8 (AFAFK), SEQ ID NO: 9 (FAKFI), SEQ ID NO: 10 (KMLIY), SEQ ID NO: 11 (KSYYY), SEQ ID NO: 12 (AKKMV), SEQ ID NO: 13 (FKFIG), SEQ ID NO: 14 (AFIPV), SEQ ID NO: 15 (KKMYY), and SEQ ID NO: 16 (AIKKK), a biologically active shuffled sequence variant, or a biologically active substitution variant, wherein (a) $P^1$ and $P^2$ may be the same or different; moreover, each occurrence of $P^1$ in the multimer may be a different one of the above peptides (or variants);

(b) X is $C_1$-$C_5$ alkyl, $C_1$-$C_5$ alkenyl, $C_1$-$C_5$ alkynyl, $C_1$-$C_5$ polyether containing up to 4 oxygen atoms, wherein m=0 or 1 and n=1-7; and wherein the peptide alone or in multimeric form has the biological activity of promoting cell attachment as described above.

When produced recombinantly, spacers are preferably $Gly_z$ as described herein, where z=1-6, and the multimers may have as many repeats of the core peptide sequence as the expression system permits, for example from two to about 12 repeats. A preferred recombinantly produced peptide multimer has the formula:

$$(P^1\text{-}Gly_z)_n\text{-}P^2$$

wherein:

(a) $P^1$ and $P^2$ are selected from the group consisting of SEQ ID NO: 1 (FIKFG), SEQ ID NO: 2 (EFIKY), SEQ ID NO: 3 (EEEKV), SEQ ID NO: 4 (GHK), SEQ ID NO: 5 (FIFAK), SEQ ID NO: 6 (KKLVY), SEQ ID NO: 7 (AFKIF), SEQ ID NO: 8 (AFAFK), SEQ ID NO: 9 (FAKFI), SEQ ID NO: 10 (KMLIY), SEQ ID NO: 11 (KSYYY), SEQ ID NO: 12 (AKKMV), SEQ ID NO: 13 (FKFIG), SEQ ID NO: 14 (AFIPV), SEQ ID NO: 15 (KKMYY), and SEQ ID NO: 16 (AIKKK), a biologically active shuffled sequence of variant, or a biologically active substitution variant, wherein (a) $P^1$ and $P^2$ may be the same or different; moreover, each occurrence of $P^1$ in the multimer may be a different one of the above peptides (or variants), wherein n=1-10 and z=0-6;

and wherein the peptide alone or in multimeric form has the biological activity of promoting cell attachment as described above.

It is understood that such multimers may be built from any of the peptides or variants described herein. Although it is preferred that the variant monomeric units of the multimer have the biological activity described above, that is not a requirement if the multimer to which they contribute has this activity.

Also included in this invention are peptides in which at least one amino acid residue and preferably only one, has been removed and a different residue inserted in its place compared to the "original" sequence that was discovered to have CAP activity. For a detailed description of protein chemistry and structure, see Schulz, G. E. et al., *Principles of Protein Structure*, Springer-Verlag, New York, 1979, and Creighton, T. E., *Proteins. Structure and Molecular Principles*, W.H. Freeman & Co., San Francisco, 1984, which are hereby incorporated by reference. The types of substitutions which may be made in the peptide molecule of the present invention are conservative substitutions and are defined herein as exchanges within one of the following groups:

1. Small aliphatic, nonpolar or slightly polar residues: e.g., Ala, Ser, Thr, Gly;
2. Polar, negatively charged residues and their amides: e.g., Asp, Asn, Glu, Gln;
3. Polar, positively charged residues: e.g., His, Arg, Lys;

Pro, because of its unusual geometry, tightly constrains the chain. Substantial changes in functional properties are made by selecting substitutions that are less conservative, such as between, rather than within, the above groups (or two other amino acid groups not shown above), which will differ more significantly in their effect on maintaining (a) the structure of the peptide backbone in the area of the substitution, (b) the charge or hydrophobicity of the molecule at the target site, or (c) the bulk of the side chain. Most substitutions according to the present invention are those that do not produce radical changes in the characteristics of the peptide molecule. Even when it is difficult to predict the exact effect of a substitution in advance of doing so, one skilled in the art will appreciate that the effect can be evaluated by routine screening assays, preferably the biological assays described below. Modifications of peptide properties including redox or thermal stability, hydrophobicity, susceptibility to proteolytic degradation or the tendency to aggregate with carriers or into multimers are assayed by methods well known to the ordinarily skilled artisan.

Peptides of the present invention may be synthesized by any suitable method known in the art, such as FMOC Chemistry of Atherton and Sheppard, 1989 in Solid Phase Peptide Synthesis (Merrifield 1965). Boc chemistry may also be used as well as synthesis on a variety of different solid supports, "tea-bag" synthesis (See, Pinilla, C et al., *Meth. Molec. Biol.*, 66:171-179 (1996)), and split and divide combinatorial methods. Solution phase methods for peptide synthesis may also be used.

As an alternative to chemical or enzymatic synthesis, the peptides of the present invention, particularly those exceeding 5 or 10 amino acids in length, are more preferably produced using recombinant methods. For recombinant production, the peptide sequence is first converted to a corresponding nucleic acid sequence which encodes the amino acid sequence of the peptide. This may be an RNA sequence which is subsequently translated to produce the peptide, or it may be a DNA sequence which is then cloned into an expression vector under the control of a promoter which enables the transcription of the DNA sequence and subsequence translation of the mRNA to produce the peptide. Many such methods for recombinant production of the desired peptide or protein sequence are well known to the practitioner and may be applied to the production of the peptides of the invention without the exercise of inventive skill. The peptides may be purified, if necessary, also using standard methods for physical, chemical and affinity separation which are well known to the practitioner.

In a preferred embodiment, the method utilizes as CAP agents combinations of peptides, preferably selected from a group of 40 different peptide members of a peptide library ("the BDT Library") that the present inventors and their colleagues developed using technology described in U.S. application Ser. No. 0992,124 filed on Nov. 19, 2001 by Campbell et al. entitled Peptides Promoting Adherence, Growth and Secretion; U.S. patent application Ser. No. 09/359,260 filed on Jul. 22, 1999 by Campbell et al. entitled Methods, Apparatus and Computer Program Products for Formulating Media;and U.S. patent application Ser. No. 09/608,892 filed on Jun. 30, 2000 by Haaland et al. entitled "Peptides for Use Culture Media." The peptides were tested for their CAP activity by covalently coupling them to a CAR surface, primarily hyaluronic acid (HA) which has been bonded to the surface of a cell culture vessel, for example, a polystyrene multiwell microplate. The HA surface alone resists cell adhesion (and therefore, growth of anchorage-dependent cells). The presence of the peptides of this invention stimulates cell attachment. In the absence of these inventive peptides, cells will not substantially attach to the CAR surface. More specifically, there may be some, insignificant amount of attachment to a CAR in the absence of the claimed peptides, but such cell attachment will be negligible in comparison the amount of cell attachment when the inventive peptides are present. Further, in the absence of the claimed peptides, cells will not substantially grow, differentiate, or survive. Similar attachment-promoting activity by peptides being screened for this function permits their classification into those that, alone or in combination, do or do not stimulate cell attachment (and, preferably subsequent growth, differentiation, etc.).

A "cell-adhesion resistant" or "cell-adhesion resistive" ("CAR") material or agent, when coated onto a solid surface, generally does not enable, and preferably inhibits or prevents cell adherence or attachment to the surface, thus creating a CAR surface. A material or agent that, when coating all or part of a polymer surface, results in cells attaching to a surface with low affinity, is also considered a CAR material or agent herein because in its presence, cell adherence or attachment to a surface is inhibited or prevented. Based on the properties of CAR materials, certain macromolecules such as proteins are also less likely to bind to a CAR surface. CAR surfaces are also known in the art as "non-fouling" surfaces because undesired materials (proteins, microorganisms, etc.) are unable or less able to "foul" the surface by adhering to it.

Suitable CAR materials include, but are not limited to, polyethylene glycol, glyme and derivatives thereof, poly-HEMA, poly-isopropylacrylamide and, preferably any of a number of polysaccharides including hyaluronic acid (HA) and alginic acid (AA). In general, highly hydrophilic substances containing a high concentration of hydroxyl groups may be used as CAR materials, either alone or in combination.

CAR materials, regions, and surfaces are discussed in further detail in U.S. patent application Ser. No. 10/259,815 by John J. Hemperly, Proliferation and Differentiation of Stem Cells Using Extracellular Matrix and Other Molecules, filed on Oct. 2, 2001, and based on U.S. Provisional Application No. 60/326,440, both of which are incorporated herein by reference in their entirety.

Preferred polymer surfaces are selected from the group consisting of polystyrene, polyethylene, polypropylene, polyethylene terephthalate, polytetrafluoroethylene, polylactide and cellulose. Silicone polymers such as polydimethylsiloxane (PDMS) are also used.

In a preferred embodiment, a CAR material, preferably HA, is bonded directly to polymeric nitrogen-containing surfaces. Examples of such surfaces are ammonia plasma-treated polymers and Primaria™-treated polystyrene (PS) surfaces. Polymeric substrates suitable for use in the invention include polystyrene, polypropylene, polyethylene terephthalate, polylactide, cellulose and the like, though polystyrene is preferred.

HA is preferably immobilized directly on plasma-treated surfaces (although other methods in the art employ an intermediate polyamine layer, e.g., polyethyleneimine, poly-D-Lysine, or poly-L-lysine, directly bound to the polymer with the HA bound to that intermediate layer). It is preferred that a layer of HA be formed directly onto the PS surface without losing its CAR characteristics. Thus, preferably, the methods and compositions of the present invention avoid the additional steps attendant to using such intermediate polymer layers.

The use of plasma techniques are familiar to those of skill in the art (see, for example, Garbassi F. et al., "Polymer Surfaces, from Physics to Technology", Wiley, Chichester, 6, 1994, and N. Inagaki "Plasma Surface Modification and Plasma Polymerization, Technomic Publishing Company, Lancaster, 1996). In the present invention, the plasma treatment process may be any process that is capable of causing nitrogen to be incorporated onto the surface of the polymer article resulting in reactive amine or other nitrogen-containing groups, including direct as well as remote plasma treatment methods. Examples of suitable plasma treatments are ones using reactive gases such as nitrogen, nitrogen oxide, nitrogen dioxide or ammonia in the gas phase, alone or in mixture with air, argon or other inert gases and may be preceded or followed by treatments employing argon or other inert gases. The plasma may be sustained over the full treatment time or may be administered in pulses. Preferably, the plasma gas is ammonia, and treatment is performed with a power charge of between I and 400 W, preferably between 10 and 150 W, a pressure between 10 mTorr and 10 torr, and a treatment time between 1 second and 1 hour, preferably between 10 seconds and 30 minutes.

Plasma-treated polystyrene can be prepared, for example by pumping the treatment chamber to a 0.3 mTorr base pressure, establishing a 200 mTorr argon atmosphere, and applying a 60 sec argon plasma treatment, followed by a 120 sec, 375 mTorr $NH_3$ plasma treatment at 95 W. Other suitable treatments will be known to those of skill in the art.

The purpose of the plasma treatment is to create a high surface concentration of covalently attached amine groups. The surface can then be reacted with HA or a derivative thereof, or alginic acid (alginate), in the presence of a condensing agent such as ethyldimethylaminopropyl carbodiimide (EDC), in aqueous solution or dicyclohexylcarbodiimide (DCC), in organic solvents. EDC activates the COO— groups present in HA, creating a reactive ester intermediate. This intermediate is highly unstable and subject to hydrolysis, leading to the cleaving off of the activated ester intermediate, forming an isourea, and regenerating the —$COO^-$ group. To stabilize this reactive intermediate, a molecule able to enhance the reaction promoted by EDC, such as N-hydroxysuccinimide (NHS), hydroxy-sulfosuccinimide (sulfo-NHS) or hydroxybenzotriazolo hydrate should also be present. Although not intended to be bound to a particular theory, it is believed that attachment of HA to the amine containing polymer surface occurs through a mechanism wherein (for example) EDC and NHS combine to create an active ester polysaccharide with a carboxyl group capable of coupling to an amine. When coupling occurs, NHS is released. Other compounds known in the art that are able to react with EDC in this manner and which serve as reactive intermediate ester stabilizing compounds should also be effective in the invention. Other plasma treatment methods for producing surfaces with amine and other nitrogen-containing groups are also suitable, and are known to those of skill in the art. Following plasma treatment of the surface to be coated, the plasma-treated surface is exposed to an aqueous solution containing HA or a derivative thereof, or AA in the presence of a carbodiimide, preferably EDC. The term "expose" or "exposing" as used herein is intended to include any type of contact made between a liquid and a solid, for example by pipetting, pouring, spraying, dripping, immersing, pouring, dipping, injecting, etc., without limitation.

A reactive intermediate ester-stabilizing compound that substantially increases the I 0 coupling yield by stabilizing the reactive intermediate formed by the carbodiimide is also present. Such compounds are generally selected from the class of N-hydroxysuccinimides and aryl or heterocyclic derivatives thereof. Preferred N-hydroxysuccinimides include, but are not limited to, NHS, sulfo-NHS, and hydroxy-benzotriazolo hydrate.

Suitable derivatives of HA that may be used in the invention will be known to the skilled artisan, and are described, for example, in U.S. Pat. No. 4,851,521 to della Valle, et al. These include partial esters of hyaluronic acid with alcohols of the aliphatic, araliphatic, cycloaliphatic and heterocyclic series and salts of such partial esters with inorganic or organic bases. Similar derivatives of alginic acid should also be useful.

Surfaces prepared as discussed above are very effective in resisting adhesion of cells and can be prepared much more economically and efficiently than those requiring an intermediate layer of a compound comprising nitrogen-containing groups (as noted above). These CAR surfaces are the "substrate" for the addition of the peptides of this invention that promote the attachment, growth, differentiation, etc., of cells.

HA is an anionic polysaccharide composed of repeating units of beta-1,4-glucuronate-beta-1,3-N-acetylglucosamine. A reactive —$CO_2^-$ group is present on every repeat unit of HA that can be utilized to covalently couple HA to an amine containing surface using methods described herein. EDC reacts with —COOH to create an active-ester (o-acylisourea) intermediate. This intermediate is highly unstable and subject to hydrolysis, leading to cleaving off the activated ester intermediate, forming an isourea, and regenerating the —COOH group. To stabilize this unstable reactive intermediate and increase reaction yield, hydroxy-sulfosuccinimide (sulfo-NHS) or another equivalent agent is added to the reaction.

HA covalently bonded to polystyrene in this way prevents attachment of any of a number of types of cells, including NIH3T3 and osteoblast MC3T3 cells which the present inventors have studied extensively.

CAR surfaces formed as described herein are useful for the same purposes as HA-coated and other CAR surfaces that were previously known in the art. When not further treated, such surfaces resist cellular attachment and growth. However, in the present invention, they are further treated by means known in the art to selectively attach peptides having desired CAP properties.

The preferred CAP surface is prepared by starting with a CAR surface, which may be one created using methods disclosed herein and in commonly assigned co-pending patent applications: U.S. patent application Ser. No. 10/259,797 by Andrea Liebmann-Vinson and R. Clark, Cell Adhesion Resisting A, Surfaces, filed on Sep. 30, 2002; U.S. patent application Ser. No. 10/259,815 by John J. Hemperly, Proliferation and Differentiation of Stem Cell from Bone Marrow and Other Cells Using Extracellular Matrix and Other Molecules, infra; and U.S. patent application Ser. No. 10/259,816 by Cheryl H. Dean et al., Peptides with Inhibitory Growth Action, filed on 9/30/2002 and based on U.S. Provisional Application 60/333,476, all of which are incorporated herein by reference in their entirety. The present CAP peptide or peptide combination is covalently bonded to the CAR surface by employing chemical reactions described below. The binding of these CAP peptides (which peptides have been found in the invention to promote cell attachment) to the CAR surface creates the CAP surface. As the newly created CAP surface was originally a CAR surface, this document also refers to a peptide-modified CAP surface as an "otherwise CAR surface" indicating that but for the addition of the CAP peptides, the surface was previously CAR. In fact, the present invention contemplates surfaces which comprises spatially arrayed CAR and CAP regions, as discussed more fully below.

Ultimately, it is the CAP peptides of the invention that define the CAP surface. The CAP peptides are those peptides, and combinations thereof, determined by the invention to promote cell attachment. As described herein (see Example 1), these peptides were determined to promote attachment and growth of certain types of adherent cells based on a comparison of cell attachment and growth in a tissue culture polystyrene (TCPS) microplate in wells coated with HA to make them CAR, and wells coated with HA to which various peptide combinations have been covalently bound. Peptide-modified surfaces, in the form of culture microwells to which the peptides are bound, are peptide combinations that (a) show a significantly higher number of attached, live cells when compared to the [TCPS+HA] "negative" control, and
(b) show equal or greater cell attachment than a "positive control" peptide that includes the RGD sequence (such as GRGDS).

Figure 3:
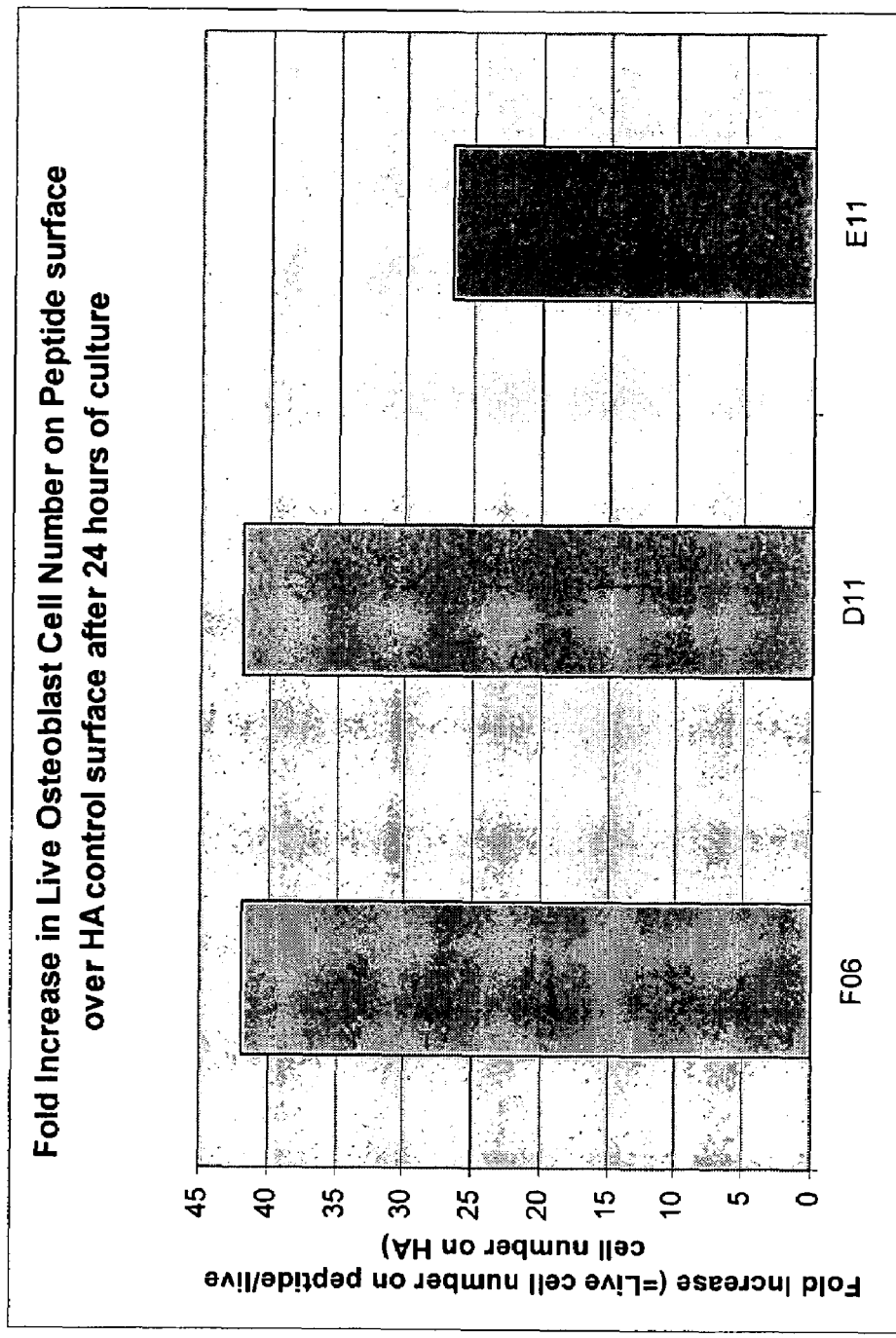
FIG. 3 is a graph showing the fold increase in live osteoblasts on peptide-modified HA surfaces compared to "HA only" CAR control surfaces after twenty-four (24) hours of culture, as described in Example 1.

For example, as disclosed in Example 1 and shown in FIG. 1, the present peptides increased growth of NIH3T3 cells by a factor of 4 compared to a well containing RGD, and even more when compared to the HA control surface. A 42-fold increase was attained using the peptides of this invention to promote attachment and growth of an osteoblast cell line (shown in FIG. 3)

Methods and cell cultures encompassed by the present invention are not to be limited to those anchorage-dependent cell lines used by the present inventors in the experiments described herein.

The peptide-modified CAP surface may be created on a polymer surface of any standard tissue culture vessel and formats such as round single dishes or cluster dishes, flasks, sheets and wells of microplates of any number and geometric layout of wells, preferably multiwell plates having 96 wells (8×12), 192 wells, 384 wells, etc.

Peptide-modified CAP surfaces are also produced on the outer and "inner" surfaces of various standard or unusual three-dimensional "structures," such as matrices or scaffolds (See, for example, commonly assigned patent applications U.S. patent application Ser. No. 10/260,737 by Mohammad A. Heidaran et al., Method and Apparatuses for the Integrated Discovery of Cell Culture Environments, filed Sep. 30, 2002; U.S. patent application Ser. No. 10/259,817; J. A. Rowley et al., 3-D Scaffold Array Platform for High Throughput Screening, filed Sep. 30, 2002.)

Furthermore, the CAP peptide-modified CAR surface is not limited to peptides covalently bound to HA immobilized to a surface; rather, the peptides may be covalently bound to other CAR surfaces (see below).

Cell Adhesion Resisting (CAR) Surfaces

CAP and CAR "Regions"

A CAR region is an area on a support surface onto which a CAR material has been placed, added, spotted, etc. The same is the case for a CAP region. A first region is "juxtaposed" to a second region if the two regions are adjacent to one another on a surface, or, are sufficiently close to one another that cells in or on the first region can respond to signals emanating from cells on the second, juxtaposed region or to a concentration gradient between two juxtaposed regions. Two juxtaposed regions may be in direct contact so that no other surface intervenes, or may be spaced at varying distances from one another. For example, two different CAP regions that are coated onto a CAR surface may abut one another or, alternatively, may be spaced so that CAR surface area that is not coated with the CAP peptides separates the two.

Any geometric relationship between CAR regions and CAP regions is included in the scope of this invention. Thus, one preferred surface is coated with a uniform CAR layer which has placed upon it, preferably bonded covalently, CAP regions that comprise a single peptide of the invention or a selected combination of agents. If different CAP regions on a surface each have a particular peptide or peptide combination, neighboring CAP regions may have different concentrations (or densities) of that peptide or combination. The CAP regions may abut one another with no spacing or may have unmodified areas of CAR surface between them.

In another embodiment, discrete CAR regions are distributed on the surface; some of these are modified with CAP peptides so that the surface includes CAR-only regions and CAP regions (on a CAR surface). Such a surface may optionally include CAP-only regions which are bound to the surface in the absence of an underlying CAR material. Such regions may be prepared on any suitable surface for use in cell culture or in cellular assays, and includes sheets, slides, dishes (e.g., petri dishes), culture flasks, multiwell cluster dishes of any number and geometric layout of wells. Preferred are multi-well plates having 96 wells, 192 wells, 384 wells, etc.

A preferred embodiment of this invention is a composition comprising CAP peptides immobilized covalently to a CAR layer on a polymer surface. An advantage of that surface is that it prevents "non-specific" cell and protein adsorption in areas not covered by the CAP peptides. Such surfaces are made by covalently bonding a peptide or peptides. This embodiment may begin with an already prepared CAR surface or may include the first modification step or steps of creating the CAR surface.

Once HA, for example, is bonded to that surface, free hydroxyl groups of the HA are oxidized to aldehydes, for example with a periodate (e.g., $NaIO_4$). The peptides can now react with these aldehyde groups through their free primary amine groups (N-terminus, Lys or Arg side chains, etc.). To stabilize the linkage between the peptide and the CAR layer, subsequent reductive alkylation of the imine moiety is carried out using reducing agents (i.e., stabilizing agents) such as, for example, sodium borohydride, sodium cyanoborohydride, and amine boranes, to form a secondary amine ($R'NH—CH_2R$). This reductive amination results in covalent bonding between the peptide and the reactive aldehydes on the saccharide rings of the HA (or AA).

Alternatively, in a reaction very similar to the binding of HA to amino groups on plasma-treated PS, the $COO^-$ groups of the CAR material, preferably HA, may be activated to form reactive intermediate esters (o-acylisourea) by the addition of EDC and the addition of NHS or an equivalent. Free amino groups of a peptide or polypeptide (N-terminus, Lys and Arg side chains, etc.) can now react with these reactive intermediate esters or the stabilized reactive intermediate esters, forming a stable amide bond. This results in covalent bonding between the peptide or polypeptide and the reactive ester on the saccharide rings of the HA or AA.

Such coupling and stabilizing reactions are carried out in a neutral or slightly basic solution and at a temperature of about 0-50° C. Preferably, the pH is about 6-10, and the temperature is about 4-37° C., for the coupling and stabilizing reactions. These reactions (coupling and stabilizing) can be allowed to proceed for just a few minutes or for many hours. Commonly, the reactions are complete (i.e., coupled and stabilized) within 24 hours.

The peptide-modified CAP surfaces of the present invention are not limited to standard tissue culture vessels and 2D surfaces, but include 3D structures and flexible materials described below.

In addition to the more traditional two-dimensional culture surfaces and vessels described above, the present invention includes the use of three-dimensional (3D) scaffolds for use in conjunction with the CAP peptides of the present invention (including for testing candidate peptides for CAP activity when they are on a CAR surface). "Three-dimensional scaffold" refers herein to a 3D porous template that may be used for initial cell attachment and subsequent tissue formation either in vitro or in vivo. A 3D scaffold according to this invention comprises base materials (described below), a CAR layer and bound thereto CAP peptides, and optionally, other substances, which promote or enhance cell attachment, growth, migration, and/or differentiation.

3D scaffolds coated with a CAR layer to which are bound CAP peptides are used in cell culture to permit cell growth and differentiation in a structural environment that more closely mimics the in vivo setting.

The 3D scaffolds used in the present invention may be of any suitable size or shape. In one embodiment, the 3D scaffolds are between about 1 to 50 mm in diameter. In another desired embodiment, the 3D scaffolds are between about 3mm to 25 mm in diameter. In a yet additional desired embodiment, the 3D scaffolds are between about 3 mm to 10 mm in diameter.

Useful 3D scaffolds have a high density of interconnected pores which guide and support cell and tissue growth. The pore structures provide physical surfaces which are coated with a CAR material and CAP peptides as described herein, though adherent cells can also lay their own 3-D ECM. Moreover, the porous structures offer improved nutrient transport to the center of the scaffold through the porous interconnecting channel network and limit the cell cluster size to prevent the formation of large cell clusters that can potentially develop into necrotic center due to lack of nutrition. Preferably, the three-dimensional scaffold used in connection with the present invention has a pore size of about 50 to 700 µm in diameter, preferably, about 75 to 300 µm in diameter. The suitable percentage of porosity in the scaffold is about 50% to 98%, and preferably, 80% to 95%.

The 3D scaffolds of the present invention comprise any suitable base material for construction of these scaffolds, including natural polymers, synthetic polymers, inorganic composites and combinations of these materials. Useful natural polymers include collagen-and glycosaminoglycans (GAG). Synthetic polymers useful for scaffolding applications include poly(α-hydroxy acids) such as polylactic acid (PLA), polyglycolic acid (PGA) and copolymers thereof (PLGA), poly(orthoesters), polyurethanes, and hydrogels, such as polyhydroxyethyl methacrylate (poly- HEMA) or polyethylene oxide-polypropylene oxide copolymer (PEO-PPO). Poly(α-hydroxy acids) are among the few synthetic degradable polymers that are approved for human clinical use and have been used extensively for sutures.

3D scaffolds may be fabricated by well-known methods. A common fabrication process for synthetic and natural scaffold materials involves phase separation. In particular, phase separation upon freeze-drying has been used extensively (e.g., Zhang et al., *J. Biomed. Mater. Res.*, 45:285-293 (1999); Ranucci et al., *Tissue Engineering* 5: 407-420, (1999); (Lu et al., *Biomaterials* 21: 1595- 1605, (2000)). The base material is dissolved in a suitable solvent and rapidly frozen. The solvent is removed by freeze-drying leaving behind a porous structure. Non-limiting examples of scaffolds fabricated from natural polymers using this technique are porous collagen sponges with pores between about 50 and about 150 µm (Pieper et al., *Biomaterials,* 20:847-858 (1999)), collagen-glycosaminoglycan (GAG) scaffolds with an average pore size ranging from about 90 µm to about 120 µm (Hem et al., *J. Biomed. Mater. Res.* 39:266-276, (1998)), chitosan hydrogels with pores ranging from about 45 µm to about 250 µm (Oxley et al. *Biomaterials* 14: 1064-1072, (1993)) and chitosan scaffolds with pore sizes ranging from about 1 µm to about 250 µm (Madihally, S. V. et al., *Biomaterials.* 21:1607-1619, (1999)) depending on freezing conditions. Examples for synthetic polymer scaffolds manufactured by freeze-drying are PLLA (poly(L-lactic acid)) foams with porosity of up to about 95% with an anisotropic tubular morphology combined with an internal ladder-like structure containing channels ranging from several tens of µm to several hundred µm in diameter (Zhang et al, supra, 1999), and PLGA (poly(DL-lactic-co-glycolic acid)) foams with about 90 to about 95% porosity and with average pore sizes ranging from about 15µm to about 35 µm together with large pores of up to about 200 µm (Whang et al. *Polymer* 36:837-842, (1995). Freeze-drying allows incorporation of small hydrophilic or hydrophobic bioactive molecules into PLLA and poly(phosphoester) scaffolds (Thomson et al., Polymer Scaffold Processing. In: *Principles of Tissue Engineering*, Lanza et al., eds., Landes Company, pp 263-272, (1997)).

Useful modifications of the freeze-drying technique are the "freeze-thaw technique" (Oxley et al., *Biomaterials* 14:1064-1072, (1993)). This technique uses phase separation between a solvent, in particular water, and a hydrophilic monomer upon freezing, followed by polymerization of the hydrophilic monomer by UV irradiation and removal of the solvent by thawing. This leads to the formation of macroporous hydrogels. A second modification is freeze-immersion precipitation in which a polymer is dissolved in a solvent, cooled, immersed in a non-solvent, brought to room temperature followed by solvent removal, as demonstrated in the fabrication of polyester-urethane foams with pore sizes ranging from about 100 µn to about 150 µm (Saad, B. et al., *J. Biomed. Res.* 32:355-366, (1996). By combining phase separation with atomization and thin film deposition, PS foams with pore sizes up to about 100 µm have been fabricated (Gutsche, A. et al., *Biomaterials* 17:387-393, (1996).

Natural polymers can be formed into networks and gels suitable for 3D culture. Crosslinking of gelatin, a protein derived from collagen, and alginate create sponges with pores ranging from about 10 µm to about 100 µm (Choi et al., *Biomaterials* 20:409-417 (1999).

Three-dimensional printing, a fabrication technique similar to stereolithography, involves selectively directing a solvent onto a polymer powder packed with NaCl particles to build complex 3D structures as a series of very thin two-dimensional slices followed by leaching of the NaCl particles in water. PLGA scaffolds with about 60% porosity and microspores ranging from about 45 µm to about 150 µm have been fabricated using this technology (Kim et al., *Ann. Surgery* 228:8-13, (1998).

Gas foaming methods involve the formation of a solid followed by exposure of this solid to a gas, e.g., $CO_2$, under high pressure which is allowed to saturate the polymer and after which the gas pressure is rapidly decreased. Pore formation occurs during pressure release due to the nucleation and expansion of the $CO_2$ dissolved in the polymer matrix. PLGA foams of porosity up to about 93% and with pore sizes of about 100 µm were prepared by this method (Mooney et al., *Biomaterials* 17:1417-1422, (1996)) reported the fabrication of PLGA foams with porosity of 97% and pore sizes ranging from about 10 μm to about 100 μm using this method.

3D scaffolds may be fabricated by any known method including, but not limited to, those described above, or may be obtained commercially. Commercially available 3D scaffolds may be obtained from, for example, New Brunswick Scientific Co, Edison, N.J. (e.g., Fibra Cel®).

The CAP peptide-modified CAR surfaces can also be in the form of a flexible material such as polydimethyl siloxane (PDMS) or other silicone-based polymer.

The present invention is also directed to cell culture systems that comprise a culture surface or vessel coated with a CAR layer and CAP peptides as described above.

Other embodiments include actual cell cultures comprising cells in a culture medium incubated in or on the above culture vessels or surfaces.

The present methods for attaching and growing cells on the modified surfaces, and the above cell cultures, may utilize any suitable culture conditions. Any culture conditions appropriate for the cell of interest may be used, including any acceptable atmosphere (e.g., humidified air supplemented with a range of concentrations of $CO_2$ or a mixture of gases that approximates air, such as known mixtures of $N_2$ and $O_2$, $CO_2$, etc.).

Any known or yet to be developed culture medium may be used. As is well-known in the art, certain media are preferred for culture of certain specialized cell types. A list of commercially available media that may be used herein is shown in the Table 1, below.

is within the skill of the art to select a preferred medium formulation for a given cell type to be used with the peptide-modified polymer surfaces described herein.

The compositions and the methods utilizing CAP peptide-modified CAR surfaces, as described herein, are applicable to the analyze the attachment, growth and/or differentiation of any adherent cell type, and may be used to culture such cells for intervals of varying duration. Example 1 below focuses on two particular cells types" (1) the almost ubiquitous NIH3T3 fibroblast cell line and (2) the more "specialized" MC3T3 osteoblast cell line. However, as intended, this invention is equally applicable to any cell type, whether (i) a primary culture of cells derived from a tissue or tumor explant, or from any body cavity or fluid, (ii) a cell type that can be maintained in culture for a limited period before senescence, or (iii) an immortalized long term cell line. Preferred types of cells include liver or liver derived cells such as primary hepatocytes, neuronal cells, neuronal stem cells, mesenchymal stem cells, pancreatic cells, skeletal muscle cells, cardiomyocytes, liver epithielial cells (a source of stem cells), HepG2 cells, a hepatocellular carcinoma-derived cells line.

As noted above, the present invention includes cell cultures comprising a CAP peptide-modified CAR surface in a culture vessel with cells and culture medium present therein. This invention permits not only discovery of optimal conditions for attachment, growth and differentiation of a cell of interest, but, once such conditions are identified, compositions and methods for optimal culture of these cells. Such cultures may be used for propagating viruses and selected microorganisms,

TABLE 1

List of Culture Media*

| | |
|---|---|
| α-Modification of Eagle's Medium | NCTC Medium |
| Click's Medium | RPMI 1640 |
| CMRL-1066 Medium | Swim's S-77 Medium |
| Eagle's Mimimum Essential Medium or Basal Medium Eagle (BME) | Waymouth Medium |
| Dulbecco's Modified Eagle's Medium (DMEM) | William's Medium E |
| DMEM/F-12/RPMI 1640 (1:1:1) w/o glutamine | BD Biosciences II-3 Culture Supplement |
| Fischer's Medium | BD Biosciences Universal ITS Culture |
| Glascow MEM | BioWhittaker Classic Cell Culture Media |
| Ham's F-10 Medium | Biowhittaker Powdered Cell Culture Media |
| Ham's F-12 Medium | Lechner & LaVeck's LHC |
| Iscove's Modified DMEM (IMDM) | Messi's FMX-8 |
| Joklik's Modified Eagle's Medium (JMEM) | Wyss' ZO |
| L-15 Medium (Leibovitz) | Mediatech Cellgro Improved MEM Media |
| Medium 199 (M199) | Mediatech Cellgro Complete |
| McCoy's 5A Modified Medium | Mediatech Cellgro |
| | BGBb Medium (Fitton-Jackson Modif |
| ChoMaster ® (line of chemically defined, protein and peptide-free minimal culture media for the cultivation of Chinese Hamster Ovary cells) | |
| InVitrus ™ (for in vitro maintenance of human T-lymphoma cell lines, mammalian kidney cell lines, and monolayers of primary chicken embryo fibroblasts in chemically defined, protein and peptide-free culture environments) | |

*Many of these media are also available commercially with various individual amino acids, vitamins, sugars, dyes, etc., omitted.

As is noted in Example 1, a certain concentration of a serum supplement such as fetal calf serum may be desired in a medium used for this invention. Other sources such as non-fetal mammalian sera, horse serum or sera of other species may be substituted. It may be preferred to use a completely defined medium without addition of a serum source. It for analyzing susceptibility of cells to infection, for screening drugs, for carrying out various genetic tests, for producing cellular products, for generating implantable artificial tissues, and the like.

Having now generally described the invention, the same will be more readily understood through reference to the following examples which are provided by way of illustration, and are not intended to be limiting of the present invention, unless specified.

EXAMPLE 1

Identification and Testing of Cell Adhesion Promoting Peptides

Thirty-nine peptides were identified by screening a peptide library ("BDT library"). One peptide, GRGDS (SEQ ID NO: 22), served as positive control that was known to facilitate cell attachment due to the presence of the RGD motif. The 40 peptides were divided into 10 groups of four (as shown in Table 2 below) and immobilized by periodate oxidation of HA, coupling of peptide in presence of cyanoborohydride to HA-surfaces of individual culture "vessels" in wells of a 96-well microplate. Each well had covalently coupled combinations of peptides as follows:

(a) a combination of four peptides listed as Groups 1-10 in Table 2.
(b) a combination of 8 peptides that was made up of two or more of Groups 1-10; or
(c) a combination of all 40 peptides of Table 2.

The cells were incubated at 37° C. in an incubator. Cell attachment was assessed at four hours, and cell growth at twenty-four hours by enumerating viable adherent cells at these times. The number or proportion of viable cells in each well was determined using an automated fluorescence system whereas a fluorescent stain, calcein, indicated viability vs. cytotoxicity. With this method, automated florescence microscopy and image analysis were used to acquire images and analyze numbers of live and dead cells. These methods are well known to persons of skill in the art. Other methods suitable for determining numbers of live cells may also be used.

Results

FIG. 1 shows the number of live attached fibroblasts after four hours of culture to covalently immobilized peptide. NIH3T3 cell attachment was maximal in well C2, which contained Factor 5 and Factor 8, when compared to control cell attachment on Tissue Culture Polystyrene Control (TCPS). (TCPS is a standard control that is well known in the art.) Attachment in well C2 exceeded attachment in those wells containing Factor 1, which includes the "positive control" RGD sequence, (a known inducer of fibroblast adhesion). The next highest level of attachment occurred in well

TABLE 2

| GROUP 1 | GRGDS (SEQ ID NO: 22) | AKIFF (SEQ ID NO: 23) | AAIKK (SEQ ID NO: 24) | IKYYY (SEQ ID NO: 25) |
|---|---|---|---|---|
| GROUP 2 | KFAFI (SEQ ID NO: 26) | FIKLM (SEQ ID NO: 27) | FFFIK (SEQ ID NO: 28) | EFIKK (SEQ ID NO: 29) |
| GROUP 3 | FIKFG (SEQ ID NO: 1) | EFIKY (SEQ ID NO: 2) | EEEKV (SEQ ID NO: 3) | GHK* (SEQ ID NO: 4) |
| GROUP 4 | FIFAK (SEQ ID NO: 5) | KKLVY (SEQ ID NO: 6) | AFKIF (SEQ ID NO: 7) | AFAFK (SEQ ID NO: 8) |
| GROUP 5 | FAKFI (SEQ ID NO: 9) | KMLIY (SEQ ID NO: 10) | KSYYY (SEQ ID NO: 11) | AKKMV (SEQ ID NO: 12) |
| GROUP 6 | QVVAK (SEQ ID NO: 30) | NTVYY (SEQ ID NO: 31) | GPVVY (SEQ ID NO: 32) | KKKK** (SEQ ID NO: 33) |
| GROUP 7 | IFFKG (SEQ ID NO: 34) | FFFIK (SEQ ID NO: 28) | GKNST (SEQ ID NO: 35) | DDEEK (SEQ ID NO: 36) |
| GROUP 8 | FKFIG (SEQ ID NO: 13) | AFIPV (SEQ ID NO: 14) | KKMYY (SEQ ID NO: 15) | AIKKK (SEQ ID NO: 16) |
| GROUP 9 | AFFKI (SEQ ID NO: 37) | AKKKT (SEQ ID NO: 38) | AADMQ (SEQ ID NO: 39) | FKLVA (SEQ ID NO: 40) |
| GROUP 10 | VFPFK (SEQ ID NO: 41) | FFHPY (SEQ ID NO: 42) | DIKPV (SEQ ID NO: 43) | KLLMV (SEQ ID NO: 44) |

*GHK (SEQ ID NO: 4) only peptide with 3 AA'S
**KKKK (SEQ ID NO: 33) only peptide with 4 AA'S Methods To identify peptides in a particular library which positively affected cell growth in cell culture, the library was screened in a growth assay. Two known cell lines, MC3T3, an osteoblast cell line, and NIH3T3, a fibroblast cell line, were used. Both cell lines were grown in the laboratory using standard cell culture techniques. Other cell lines available to those of skill in the art should produce similar results.

To test a peptide combination for activity, a fixed number of cells was added to each HA-coated well in medium (here DMEM) supplemented with 2% FCS.

F2, which contained Factor 1 together with Factor 5. Well E11 had Factor 1 alone. It was observed that the addition of Factor 5 to well F2 promoted more adhesion than that accounted for by the RGD peptide member of Factor 1 in well E11 alone. Because the combination of Factor 5 and Factor 8 in well C2 stimulated even more cell attachment, despite the absence of an RGD peptide, it was concluded that the adhesion promoting peptides for these cells were present in both Factors 5 and 8.

Figure 2:
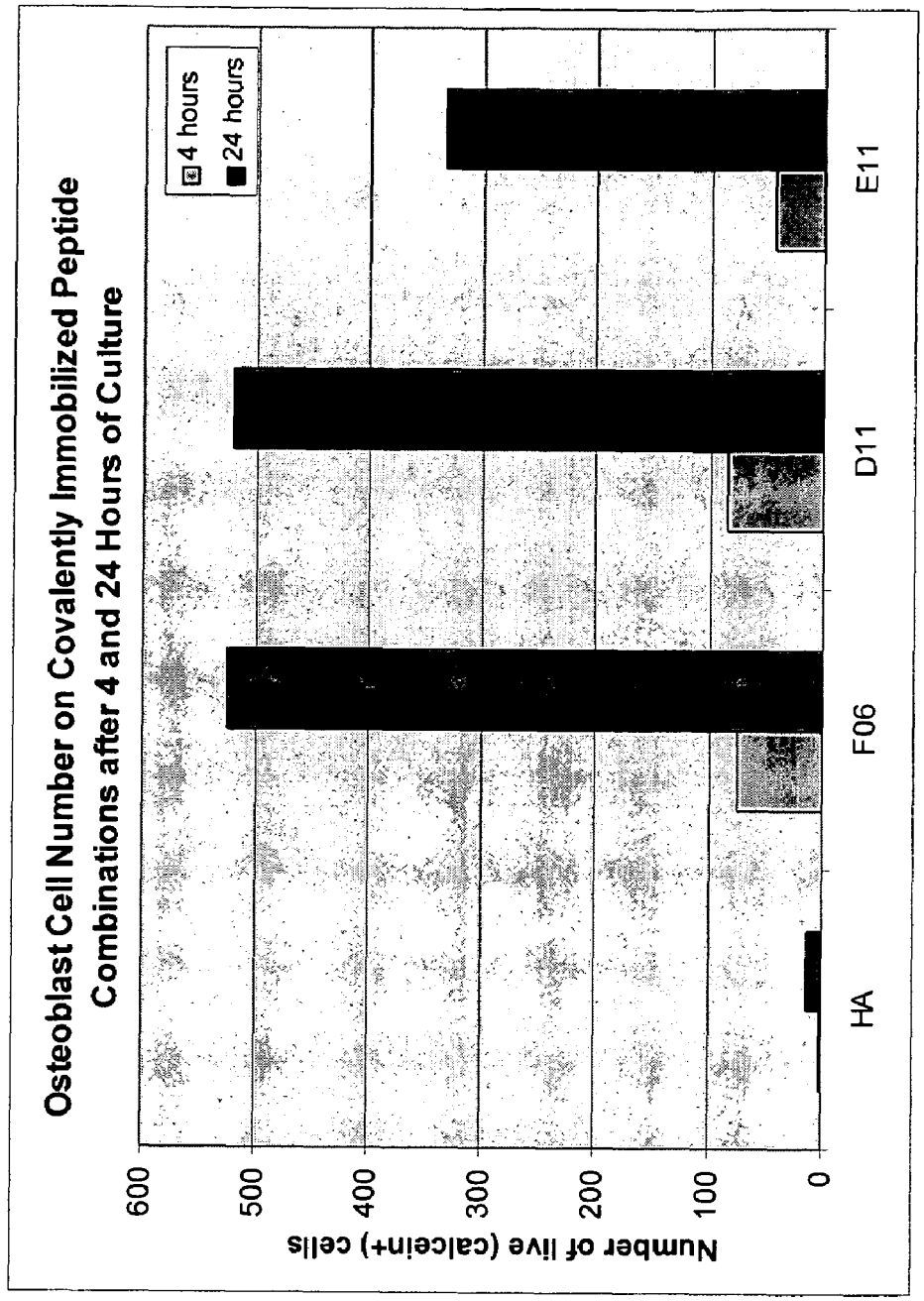
FIG. 2 is a graph showing the number of live osteoblasts (MC3T3) attached to surfaces of HA-coated plates to which were immobilized (covalently) various combinations of peptides as described in Example 1. Cells were assessed after four (4) or twenty-four (24) hours of culture.

FIG. 2 shows the number of live osteoblast (MC3T3) cells on various covalently immobilized peptide combinations at four and twenty-four hours. Osteoblast attachment at four hours in wells having both cells and peptide combinations was significantly less than the TCPS control. At 24 hours, MC3T3 cell numbers in two treatment conditions, well F6 with Factors 1 and 3 and well D11 with Factors 1 and 4, resembled the TCPS control. Notably, both these wells included the RGD peptide, yet these wells had more adherent cells than did well E1 with the Factor 1 alone. This attachment/growth-promoting effect of Factor 3; and Factor 4 independently was attributed to a synergy between an RGD peptide and one or more of the 8 peptides that comprise the factors (all of which originated from the BDT library).

Thus, the present invention identifies the following peptides as having cell attachment and growth promoting ability: SEQ ID NO: 1 (FIKFG), SEQ ID NO: 2 (EFIKY), SEQ ID NO: 3 (EEEKV), SEQ ID NO: 4 (GHK), SEQ ID NO: 5 (FIFAK), SEQ ID NO: 6 (KKLVY), SEQ ID NO: 7 (AFKIF), SEQ ID NO: 8 (AFAFK), SEQ ID NO: 9 (FAKFI), SEQ ID NO: 10 (KMLIY), SEQ ID NO: 11 (KSYYY), SEQ ID NO: 12 (AKKMV), SEQ ID NO: 13 (FKFIG), SEQ ID NO: 14 (AFIPV), SEQ ID NO: 15 (KKMYY), and SEQ ID NO: 16 (AIKKK).

EXAMPLE 2

39 peptides were identified with the BioTherapy peptide screen using media optimization technology as disclosed herein. As in Example 1, the GRGDS (SEQ ID NO:22) peptide sequence served as a positive control. Peptides were chosen based on biological activity for either cell secretion of, for example, various growth factors or proteins, or cell adhesion.

The 39 peptides and GRGDS (SEQ ID NO:22) were immobilized on 60 wells as in Example 1. In the experiments either single peptides or combinations thereof, selected from Factors 4 and 5 (see Table 2) were added to each well.

Hyaluronic acid (HA) was used to create an inert coating on a PS surface as described herein above and in U.S. patent application Ser. 10/259,797. Then bioconjuguation techniques such as sodium periodate oxidation and reductive amination disclosed herein were used to covalently couple peptide(s) to the inert HA. Any noncovalently attached peptide(s) were removed by a salt-acid wash and vigorous water rinse.

Other suitable materials that can be used as an alternative to HA, such as alginic acid, are discussed herein above. Other non-adhesive surfaces, such as poly-HEMA or PEG, that can be used to couple ECM proteins are also described.

The above process creates a cell adhesion resistant (CAR surface) with one or more peptides covalently attached.

Methods

Commercially provided rat primary hepatocytes from Xenotech (Hepatoch, Inc) were seeded at 20,000 cells/well in fully supplemented BD Hepato-STIM™ commercial media (BD Biosciences, BD Discovery Labware) with 2% fetal bovine serum on plates containing either a single peptide, or a combination of peptides covalently attached to a CAR surface. The plates were incubated overnight in $CO_2$ at 37° C. for 5 days. Medium was changed every other day by replacing half of the volume of old medium with fresh medium.

The plates were assayed on days 1 and 7 in triplicate and three assays were performed on each plate: CYP 1A1/1A2 activity assay, picogreen DNA assay for cell counting, and enzyme-linked immunosorbent assay (ELISA) for albumin secretion. CYP, or Cytochrome P450, is a group of enzymes that remove toxins from the liver and whose function is critical to healthy cells. 1A1/1A2 refers to the type of CYP enzyme for which activity the assay was used to detect. Presence of CYP activity indicates healthy, thriving cells. Albumin is a protein manufactured by the liver that performs many functions, such as maintaining osmotic pressure. Like CYP, a high level of albumin is an indication of healthy cells. CYP and albumin activity are typically lost within three days of culture, so the presence of activity on day 7 indicates functioning cells.

CYP1A 1/A2 Activity Assay and Cell Enumeration with Picogreen Assay

All media was transferred to separate plates and media samples were frozen at −20° C. until ELISA assays for albumin secretion could be performed (see below). 5 uM 7-ethoxyresorufin +80 uM dicumerol was added to all wells with cells and read at intervals for 30 min on a BMG Polarstar at excitation=540 nm and emission=590 nm to detect CYP1A1/1A2 activity. (For a more detailed discussion of this method, see Fry J R, Wiebkin P, Bridges J W, Phenobarbitone induction of microsomal mono-oxygenase activity in primary cultures of adult rat hepatocytes. Biochem Soc Trans. 1979 Feb.; 7(1): 119-21; Donato M T, Gomez-Lechon M J, Castell J V, A microassay for measuring cytochrome P4501A1 and P45011B1 activities in intact human and rat hepatocytes cultured on 96-well plates. Anal Biochem. 1993 Aug. 15;213(1): 29-33.) Cell number was determined using Picogreen™ DNA dsDNA Quantitation Kit from Molecular Probes (cat. # P7589).

Data is presented as the average number of live cells using three replicate plates from three different experiments. The experiments using peptides bound to HA were performed using 2 separate liver preparations of rat primary hepatocytes, with the exception of individual peptide experiments, which were performed once. The controls used in the CYP assay were cells on Matrigel, cells on TCPS, and 7 ethoxyresorufin alone (without cells) as a negative control.

Albumin ELISA assays

To measure albumin secretion, Probind Assay plates (Falcon 353915) were coated with 2 ug/ml Sheep IGG Anti-rat albumin antibodies, (unconjugated, Cappel cat # 55729) in a bicarbonate buffer (pH=9.6) and allowed to incubate overnight at 4° C. Antibody plates were washed three times with PBS Tween 20 and blocked with 1% gelatin (Type B, 75 bloom, Sigma cat #G6650) in PBS Tween 20 for 30 min at 37° C. Blocking solution was rinsed off three times with PBS Tween 20 and 1:400 diluted albumin/media samples from peptides screens were added along with a rat albumin (Purified Rat Albumin, Cappel cat #55952) standard curve (serially diluted 1:2 from 50 ng/ml to 1.56 ng/ml with duplicates for each dilution).

Plates were incubated 1 hr at 37° C. The plates were washed three times with PBS Tween 20 and conjugated antibody (peroxidase conjugated Sheep IGG Anti-rat albumin antibodies, Cappel #55776 diluted 1:500 from 36.6 mg/ml) was added to all wells in the antibody plate. The plates were incubated again at 37° C. for 1 hr, then washed again three times with PBS Tween 20. 0.25 mg/ml of ABTS substrate for peroxidase (Sigma #A9941) was added to a citrate substrate buffer (pH 5.0) with 0.01% hydrogen peroxide and then added to antibody plates for color development for 40 min at room temperature in the dark. The peroxidase reaction was stopped with 0.32% sodium fluoride solution and absorbance was read at 405 nm using a BMG Optima plate reader.

Wells containing both individual peptides and combinations of peptides covalently attached to HA were assayed and compared to control wells containing cells on Matrigel, cells on TCPS, and an ELISA background (no cells) as a negative control.

Results

Table 3 summarizes the effects of individual peptides on their ability to promote attachment and their ability to maintain albumin secretion and CYP activity.

TABLE 3

Summary of Effect of Individual Peptides on Primary Hepatocytes

| | Attachment | Maintains Albumin Function | Maintains CYP Function |
|---|---|---|---|
| FIFAK SEQ ID NO:5 | Yes | Yes | Yes |
| AFKIF SEQ ID NO:7 | Yes | Yes | Yes |
| FAKFI SEQ ID NO:9 | Yes | Yes | Yes |
| KKLVY SEQ ID NO:6 | Yes | Yes | Yes |
| KMLIY SEQ ID NO:10 | Yes | Yes | Low |
| AFAFK8 SEQ ID NO:8 | Loose | Yes | Low |
| AKKMV SEQ ID NO:12 | Loose | Yes | Low |
| KSYYY SEQ ID NO:11 | Loose | Yes | Low |

FIG. 4 illustrates CYP activity on Day 7 of cells on CAR surfaces containing covalently linked individual peptides. The results show that certain specific single peptides can maintain CYP activity in primary hepatoctyes significantly better than cells on standard tissue culture polystyrene. Further, the activity approaches 50% of a complex biological mixture, Matrigel™. This is significant because Matrigel is a highly complex mixture with numerous components such as extracellular matrix proteins and growth factors. Therefore, the ability of a single peptide to achieve nearly half the activity of a combination of these factors is surprising.

FIG. 5 illustrates albumin secretion on Day 7. The data indicates that certain specific single peptides can maintain albumin secretion significantly better than cells on standard tissue culture polystyrene, and have comparable or better albumin secretion compared to cells on a complex biological mixture, Matrigel™. Elisa background is the absorbance of the colorimetric reagent when no cells are present.

FIG. 6 illustrates that peptides from FIG. 4 one can be used in combinations of two, four or eight peptides with no appreciable loss of CYP activity.

FIG. 7 illustrates that peptides from FIG. 2 one can be used in combinations of two, four or eight peptides with no appreciable loss of albumin secretion.

All the references, patents, and patent applications cited above are incorporated herein by reference in their entirety, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

That which is claimed:

1. A cell culture vessel for culturing adherent cells, said vessel comprising a polymer surface, a hyaluronic acid (HA) layer bonded to said polymer surface, and one or more peptides covalently bound to the HA layer, wherein said peptides promote adherence of cells that do not adhere to the HA layer in the absence of said peptides, and wherein each of said one or more peptides comprises:

(a) one or more peptide sequences selected from the group consisting of SEQ ID NO:2 (EFIKY), SEQ ID NO:3 (EEEKV), SEQ ID NO:4 (GHK), SEQ ID NO:6 (KKLVY), SEQ ID NO:8 (AFAFK), SEQ ID NO:10 (KMLIY), SEQ ID NO:11 (KSYYY), SEQ ID NO:12 (AKKMV), SEQ ID NO:14 (AFIPV), SEQ ID NO:15 (KKMYY), and SEQ ID NO:16 (AIKKK);

(b) a chemically or recombinantly prepared peptide multimer that includes at least two repeats of any one or a combination of SEQ ID NOs:2-4, 6, 8, 10-12, and 14-16; or (c) a cell adhesion promoting variant of any one or more of SEQ ID NOs:2-4, 6, 8, 10-12, and 14-16, said variant having a conservative substitution of a single amino acid residue, wherein said variant has the ability to promote cell attachment or growth.

2. The cell culture vessel of claim 1, wherein said cells are fibroblasts or osteoblasts.

3. The cell culture vessel of claim 1, wherein said cells are liver cells.

4. The cell culture vessel of claim 1, wherein said cells are human or rat primary hepatocytes or porcine hepatocytes.

5. The cell culture vessel of claim 1, wherein said cell culture vessel is a multiwell plate.

6. The cell culture vessel of claim 1, wherein said polymer surface is formed from a flexible material.

7. The system cell culture vessel of claim 1, wherein said polymer surface is selected from the group consisting of polystyrene, polypropylene, polyethylene tereplithalate, polylactide, cellulose, and combinations thereof.

8. The cell culture vessel of claim 7, wherein said polymer surface is polystyrene.

9. A cell culture vessel for culturing adherent liver cells, said vessel comprising a polymer surface, a cell adhesion resistant (CAR) material bonded to said polymer surface, and one or more peptides covalently bound to the CAR material, wherein said peptides promote adherence of liver cells that do not adhere to the CAR material in the absence of said peptides, and wherein each of said one or more peptides comprises:

(a) one or more peptide sequences selected from the group consisting of SEQ ID NO:2 (EFIKY), SEQ ID NO:3 (EEEKV), SEQ ID NO:4 (GHK), SEQ ID NO:6 (KKLVY), SEQ ID NO:8 (AFAFK), SEQ ID NO:10 (KMLIY), SEQ ID NO: 11 (KSYYY), SEQ ID NO:12 (AKKMV), SEQ ID NO:14 (AFIPV), SEQ ID NO:15 (KKMYY), and SEQ ID NO:16 (AIKKK);

(b) a chemically or recombinantly prepared peptide multimer that includes at least two repeats of any one or a combination of SEQ ID NOs:2-4, 6, 8, 10-12, and 14-16; or (c) a cell adhesion promoting variant of any one or more of SEQ ID NOs:2-4, 6, 8, 10-12, and 14-16, said variant having a conservative substitution of a single amino acid residue, wherein said variant has the ability to promote liver cell attachment or growth.

10. The cell culture vessel of claim 9, wherein said cell adhesion resistant (CAR) material is selected from the group consisting of hyaluronic acid (HA), alginic acid (AA), polyhydroxyethyl methacrylate (Poly-HEMA), polyethylene glycol (PEG), glyme, polyisopropylacrylamide, and combinations thereof.

11. The cell culture vessel of claim 10, wherein said cell adhesion resistant (CAR) material is hyaluronic acid (HA).

12. The cell culture vessel of claim 9 wherein said liver cells are human or rat primary hepatocytes or porcine hepatocytes.

13. The cell culture vessel of claim 9, wherein said cell culture vessel is a multiwell plate.

14. The cell culture vessel of claim 9, wherein said polymer surface is formed from a flexible material.

15. The cell culture vessel of claim 9, wherein said polymer surface is selected from the group consisting of polystyrene, polypropylene, polyethylene terephthalate, polylactide, cellulose, and combinations thereof.

16. The cell culture vessel of claim 15, wherein said polymer surface is polystyrene.

* * * * *

UNITED STATES PATENT AND TRADEMARK OFFICE
CERTIFICATE OF CORRECTION

PATENT NO. : 7,399,630 B2  Page 1 of 1
APPLICATION NO. : 11/604530
DATED : July 15, 2008
INVENTOR(S) : Guarino It is certified that error appears in the above-identified patent and that said Letters Patent is hereby corrected as shown below:

Title page, (75) Inventors: should read:

--Richard David Guarino, Holly Springs, NC (US); Bryce Nelson Chaney, Durham, NC (US); Andrea Liebmann-Vinson, Willow Springs, NC (US); Perry D. Haaland, Chapel Hill, NC (US); Mohammad A. Heidaran, Cary, NC (US)--

Signed and Sealed this

Fourth Day of November, 2008

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,399,630 B2 |
| APPLICATION NO. | : 11/604530 |
| DATED | : July 15, 2008 |
| INVENTOR(S) | : Guarino |

It is certified that error appears in the above-identified patent and that said Letters Patent is hereby corrected as shown below:

Title page, (75) Inventors: should read:

--Richard David Guarino, Holly Springs, NC (US); Bryce Nelson Chaney, Durham, NC (US); Andrea Liebmann-Vinson, Willow Springs, NC (US); Perry D. Haaland, Chapel Hill, NC (US); Mohammad A. Heidaran, Cary, NC (US)--

Signed and Sealed this

Second Day of December, 2008

JON W. DUDAS
*Director of the United States Patent and Trademark Office*